US012597517B2

(12) United States Patent
Cho et al.

(10) Patent No.: US 12,597,517 B2
(45) Date of Patent: Apr. 7, 2026

(54) METHOD FOR EXTRACTING INTRINSIC PROPERTIES OF CANCER CELLS FROM GENE EXPRESSION PROFILES OF CANCER PATIENTS AND DEVICE FOR THE SAME

(71) Applicant: KOREA ADVANCED INSTITUTE OF SCIENCE AND TECHNOLOGY, Daejeon (KR)

(72) Inventors: Kwang-Hyun Cho, Daejeon (KR); Dongsan Kim, Daejeon (KR)

(73) Assignee: KOREA ADVANCED INSTITUTE OF SCIENCE AND TECHNOLOGY (KR)

(*) Notice: Subject to any disclaimer, the term of this patent is extended or adjusted under 35 U.S.C. 154(b) by 1015 days.

(21) Appl. No.: 17/163,459

(22) Filed: Jan. 31, 2021

(65) Prior Publication Data

US 2021/0241911 A1     Aug. 5, 2021

(30) Foreign Application Priority Data

Jan. 31, 2020     (KR) ........................ 10-2020-0011884

(51) Int. Cl.
    *G16H 50/20*     (2018.01)
    *G06F 18/2133*     (2023.01)
    *G16B 40/20*     (2019.01)
    *G16H 10/40*     (2018.01)

(52) U.S. Cl.
    CPC ......... *G16H 50/20* (2018.01); *G06F 18/2133* (2023.01); *G16B 40/20* (2019.02); *G16H 10/40* (2018.01)

(58) Field of Classification Search
    None
    See application file for complete search history.

(56) References Cited

U.S. PATENT DOCUMENTS

| | | | | |
|---|---|---|---|---|
| 8,332,165 | B1* | 12/2012 | Tat | ........................ G01N 29/043 |
| | | | | 702/39 |
| 2018/0251849 | A1* | 9/2018 | Newberg | ............... G01N 33/48 |
| 2019/0034400 | A1* | 1/2019 | Alda | ........................ G06F 9/54 |
| 2019/0286982 | A1* | 9/2019 | Ambai | ..................... G06N 3/04 |
| 2020/0402660 | A1* | 12/2020 | Chakravarthy | ........ G16H 50/30 |

FOREIGN PATENT DOCUMENTS

| | | |
|---|---|---|
| KR | 1020140183097 | 12/2014 |
| KR | 1020160144297 | 12/2016 |
| KR | 1020180055787 | 5/2018 |

OTHER PUBLICATIONS

O. Ahmed and A. Brifcani, "Gene Expression Classification Based on Deep Learning," 2019 4th Scientific International Conference Najaf (SICN), Al-Najef, Iraq, 2019, pp. 145-149. (Year: 2019).*

* cited by examiner

*Primary Examiner* — Robert A Sorey

(74) *Attorney, Agent, or Firm* — Kaplan Breyer Schwarz LLP

(57) ABSTRACT

Provided is a method of predicting a condition of a patient, including decomposing an input matrix to produce a residual matrix, the input matrix representing patients and expression levels of genes of the patients, training a classifier by using health condition values the patients as learning criteria and inputting the residual matrix into the classifier, and obtaining a value for predicting a health condition of a first patient, by inputting a first input matrix including the expression levels of genes of the first patient into the classifier, the first residual matrix being a residual matrix obtained from the first input matrix by using the predetermined algorithm.

9 Claims, 12 Drawing Sheets

FIG. 8A

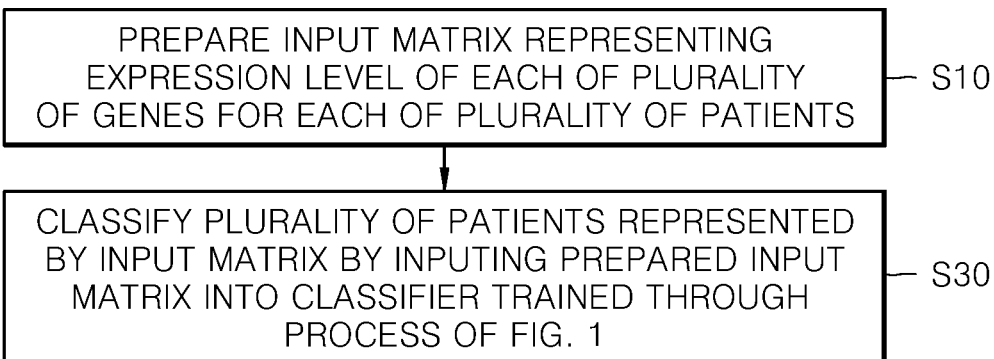

PREPARE INPUT MATRIX REPRESENTING
EXPRESSION LEVEL OF EACH OF PLURALITY
OF GENES FOR EACH OF PLURALITY OF PATIENTS   — S10

CLASSIFY PLURALITY OF PATIENTS REPRESENTED
BY INPUT MATRIX BY INPUTING PREPARED INPUT
MATRIX INTO CLASSIFIER TRAINED THROUGH
PROCESS OF FIG. 1   — S30

FIG. 8B

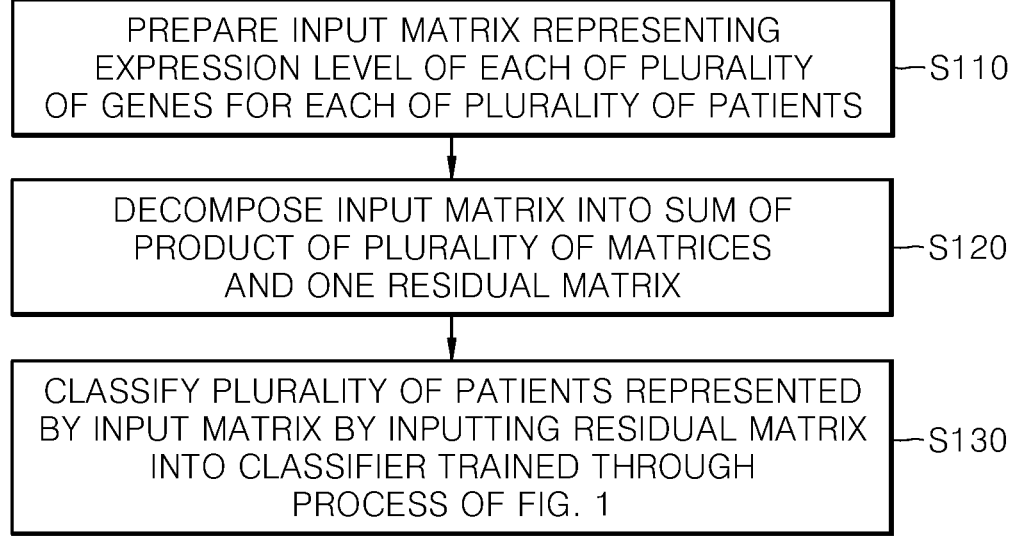

PREPARE INPUT MATRIX REPRESENTING
EXPRESSION LEVEL OF EACH OF PLURALITY
OF GENES FOR EACH OF PLURALITY OF PATIENTS   —S110

DECOMPOSE INPUT MATRIX INTO SUM OF
PRODUCT OF PLURALITY OF MATRICES
AND ONE RESIDUAL MATRIX   —S120

CLASSIFY PLURALITY OF PATIENTS REPRESENTED
BY INPUT MATRIX BY INPUTTING RESIDUAL MATRIX
INTO CLASSIFIER TRAINED THROUGH
PROCESS OF FIG. 1   —S130

FIG. 11

| 5131 | 5132 | 5133 |
|---|---|---|
| GROUP A | GROUP B | GROUP C |
| SITE 1 OF PATIENT 1, | SITE 1 OF PATIENT 2, | SITE 1 OF PATIENT 6, |
| SITE 2 OF PATIENT 1, | SITE 2 OF PATIENT 2, | SITE 2 OF PATIENT 6, |
| SITE 3 OF PATIENT 1, | SITE 3 OF PATIENT 2, | SITE 3 OF PATIENT 6, |
| SITE 1 OF PATIENT 3, | SITE 1 OF PATIENT 4, | SITE 1 OF PATIENT 8, |
| SITE 2 OF PATIENT 3, | SITE 2 OF PATIENT 4, | SITE 2 OF PATIENT 8, |
| SITE 3 OF PATIENT 3, | SITE 3 OF PATIENT 4, | SITE 3 OF PATIENT 8, |
| SITE 1 OF PATIENT 5, | SITE 1 OF PATIENT 7, | SITE 1 OF PATIENT 9, |
| SITE 2 OF PATIENT 5, | SITE 2 OF PATIENT 7, | SITE 2 OF PATIENT 9, |
| SITE 3 OF PATIENT 3, | SITE 3 OF PATIENT 7, | SITE 3 OF PATIENT 9, |
| . | . | . |
| . | . | . |
| . | . | . |

FIG. 12A

| | A | B | C | D | E | F | G | H | I | J | K | L | N | O | P | Q | R | S | T | U | V | W | X | Y |
|---|---|---|---|---|---|---|---|---|---|---|---|---|---|---|---|---|---|---|---|---|---|---|---|---|
| RS1 | 1 | 2 | 1 | 0 | 2 | 0 | 0 | 3 | 0 | 1 | 1 | 1 | 0 | 0 | 0 | 0 | 0 | 0 | 3 | 0 | 1 | 2 | 0 | 0 |
| RS2 | 0 | 1 | 2 | 1 | 1 | 0 | 0 | 0 | 3 | 0 | 0 | 2 | 3 | 3 | 0 | 0 | 0 | 0 | 0 | 3 | 2 | 0 | 2 | 0 |
| RS3 | 0 | 0 | 0 | 2 | 0 | 0 | 3 | 0 | 0 | 0 | 0 | 0 | 0 | 0 | 3 | 3 | 1 | 3 | 0 | 0 | 0 | 0 | 1 | 3 |
| RS4 | 2 | 0 | 0 | 0 | 0 | 3 | 0 | 0 | 0 | 2 | 2 | 0 | 0 | 0 | 0 | 0 | 0 | 0 | 0 | 0 | 0 | 1 | 0 | 0 |
| Q1 | N | N | N | N | N | Y | Y | Y | Y | N | N | N | Y | Y | Y | Y | N | Y | Y | Y | N | N | N | Y |
| Q2 | Y | Y | Y | Y | Y | Y | Y | Y | Y | Y | Y | Y | Y | Y | Y | Y | Y | Y | Y | Y | Y | Y | Y | Y |

FIG. 12B

| | A | B | C | D | E | F | G | H | I | J | K | L | N | O | P | Q | R | S | T | U | V | W | X | Y |
|---|---|---|---|---|---|---|---|---|---|---|---|---|---|---|---|---|---|---|---|---|---|---|---|---|
| CMS1 | 0 | 0 | 0 | 0 | 1 | 1 | 0 | 0 | 2 | 0 | 0 | 1 | 0 | 0 | 0 | 2 | 0 | 0 | 0 | 0 | 3 | 0 | 0 | 3 |
| CMS2 | 0 | 1 | 1 | 0 | 2 | 1 | 0 | 2 | 0 | 2 | 2 | 0 | 0 | 3 | 2 | 0 | 0 | 1 | 1 | 3 | 0 | 3 | 1 | 0 |
| CMS3 | 1 | 0 | 1 | 1 | 0 | 0 | 1 | 0 | 1 | 0 | 0 | 0 | 1 | 0 | 0 | 0 | 2 | 0 | 0 | 0 | 1 | 0 | 0 | 0 |
| CMS4 | 2 | 2 | 1 | 2 | 0 | 1 | 2 | 1 | 0 | 1 | 1 | 2 | 2 | 0 | 1 | 1 | 1 | 2 | 2 | 0 | 0 | 0 | 2 | 0 |
| Q1 | N | N | N | N | N | N | N | N | N | N | N | N | N | Y | N | N | N | N | N | Y | N | Y | N | Y |
| Q2 | Y | Y | N | Y | Y | N | Y | Y | Y | Y | Y | Y | Y | Y | Y | Y | Y | Y | Y | Y | Y | Y | Y | Y |

FIG. 12C

| | A | B | C | D | E | F | G | H | I | J | K | L | N | O | P | Q | R | S | T | U | V | W | X | Y |
|---|---|---|---|---|---|---|---|---|---|---|---|---|---|---|---|---|---|---|---|---|---|---|---|---|
| CRISA | 2 | 0 | 3 | 1 | 0 | 0 | 1 | 0 | 3 | 0 | 0 | 1 | 3 | 0 | 0 | 2 | 1 | 0 | 0 | 0 | 2 | 0 | 0 | 0 |
| CRISB | 0 | 0 | 0 | 2 | 2 | 0 | 1 | 0 | 0 | 0 | 0 | 0 | 0 | 0 | 2 | 0 | 1 | 1 | 0 | 0 | 0 | 0 | 1 | 3 |
| CRISC | 1 | 1 | 0 | 0 | 2 | 0 | 0 | 2 | 0 | 0 | 3 | 0 | 0 | 0 | 0 | 0 | 1 | 0 | 2 | 0 | 0 | 3 | 0 | 0 |
| CRISD | 0 | 1 | 0 | 0 | 1 | 3 | 0 | 0 | 0 | 3 | 0 | 2 | 0 | 0 | 0 | 0 | 0 | 0 | 1 | 0 | 1 | 0 | 0 | 0 |
| CRISE | 0 | 1 | 0 | 0 | 0 | 0 | 1 | 1 | 0 | 0 | 0 | 0 | 0 | 3 | 1 | 1 | 0 | 2 | 0 | 3 | 0 | 0 | 2 | 0 |
| Q1 | N | N | Y | N | N | Y | N | N | Y | Y | Y | N | Y | Y | N | N | N | N | N | N | N | Y | N | Y |
| Q2 | Y | N | Y | Y | Y | Y | N | Y | Y | Y | Y | Y | Y | Y | Y | Y | N | Y | Y | Y | Y | Y | Y | Y |

METHOD FOR EXTRACTING INTRINSIC PROPERTIES OF CANCER CELLS FROM GENE EXPRESSION PROFILES OF CANCER PATIENTS AND DEVICE FOR THE SAME

CROSS-REFERENCE TO RELATED APPLICATION

This application claims priority to Korean Patent Application No. KR 10-2020-0011884 filed on Jan. 31, 2020 and all the benefits accruing therefrom under 35 U.S.C. § 119, the contents of which are incorporated by reference in their entirety.

BACKGROUND

The present disclosure relates to a variety of fields including complex network science, systems biology, network medicine, systems pharmacology, and computational biology. The present disclosure relates to a method of classifying a condition of a patient by using computing technology.

A condition of a cancer patient may be classified by collecting a part of a body of the patient and analyzing expression levels of genes. The condition of the patient may be classified into, for example, group A having a good prognosis after cancer treatment, group B having a moderate prognosis, and group C having a poor prognosis.

The prognosis of a specific patient 1 may be checked by actually analyzing the health condition of patient 1, and in this case, the analyzed value may be regarded as the correct answer for the prognosis. Meanwhile, the prognostic value of patient 1 may be predicted through genetic analysis of patient 1. In this case, if the correct answer value and the predicted prognostic value match, a prediction algorithm through genetic analysis may be considered to be reliable. For example, when patient 1 is predicted to belong to group A through the genetic analysis, if the correct answer value obtained by actually observing the prognosis of patient 1 falls within the range of group A, the prediction algorithm may be considered to be reliable.

However, when samples are collected from the body of patient 1 for the genetic analysis of patient 1, there is a limitation in that the gene expression profile obtained may vary depending on the collecting location. That is, if a sample is collected from a part of the body of patient 1 that contains no or fewer cancer cells and genetic analysis is performed on the sample, the predicted prognosis value of patient 1 is highly likely to be good; in contrast, if the sample is collected from a part that contains a lot of cancer cells and genetic analysis is performed on the sample, the predicted prognosis value of patient 1 is highly likely to be bad. As described above, due to the fact that the prediction result for the prognostic value varies depending on the site of the patient's body at which the gene expression profile has been obtained, there is a limitation in that it may not be possible to provide a consistent prognostic value for individual patients. Therefore, a technology is required that is capable of reliably predicting the prognostic value after cancer treatment regardless of the site of the patient's body collected for genetic analysis.

SUMMARY

The present disclosure provides a technology that is capable of reliably predicting the prognostic value regardless of the site of the patient's body collected for genetic analysis. That is, the present disclosure provides a new technology for classifying patients by using residual information obtained by modifying gene expression level information of patients.

In accordance with an exemplary embodiment, a method of predicting a condition of a patient includes: decomposing, by a computing device, an input matrix (110) into a sum of a product of a plurality of element matrices (111, 112) and one residual matrix (120) by using a predetermined algorithm, the input matrix representing expression levels of a plurality of genes of a plurality of patients and each of the patients; training, by the computing device, a classifier (20) by supervised learning by using a plurality of health condition values representing health conditions of the plurality of patients as learning criteria and inputting the residual matrix into the classifier, in order to train the classifier (20) receiving a matrix having the same dimension as the residual matrix by the supervised learning; and obtaining, by the computing device, a value for predicting a health condition of a first patient, by inputting a first input matrix including the expression levels of genes of the first patient of which a health condition is required to be predicted into the classifier or inputting a first residual matrix into the classifier, the first residual matrix being a residual matrix obtained from the first input matrix by using the predetermined algorithm.

The predetermined algorithm may be a non-negative matrix factorization algorithm.

The classifier may be trained by the supervised learning to classify the plurality of patients by receiving the residual matrix and assigning indexes representing different patients included in the input residual matrix to predetermined groups.

Each row of the input matrix and the residual matrix may represent a different gene, and each column of the input matrix may represent a different patient.

Each row of the input matrix may represent a different gene, and each column of the input matrix may represent a different test sample collected from bodies of the patients, and when patients represented by two different columns of the input matrix are the same patient, the two different columns may be test samples collected from different sites of a body of the same patient.

The plurality of element matrices may include a total of two element matrices, and the input matrix may be the same as a matrix obtained by adding the residual matrix to a product of the two element matrices.

In accordance with another exemplary embodiment, a computing device includes: a residual generation unit (10) configured to output one residual matrix by receiving an input matrix (110) representing the plurality of patients and expression levels of a plurality of genes of each of the patients and decomposing the input matrix into a sum of a product of a plurality of element matrices (111, 112) and the residual matrix (120); a classifier (20) configured to receive a matrix having the same dimension as the residual matrix; and a processing unit. In this case, the processing unit is configured to train a classifier (20) by supervised learning by using a plurality of health condition values representing health conditions of the plurality of patients as learning criteria and inputting the residual matrix into the classifier (20), in order to train the classifier (20) by the supervised learning; and obtain a value for predicting a health condition of a first patient, by inputting a first input matrix into the classifier or inputting a first residual matrix into the classifier, the first input matrix including the expression levels of genes of the first patient of which a health condition is required to be predicted, the first residual matrix being a residual matrix obtained from the first input matrix by using the predetermined algorithm.

The computing device may further include a user interface (340), and sizes of the plurality of element matrices may be adjusted according to a parameter value input through the user interface.

The residual generation unit (10) may include an equator (11), and the equator may be configured to decompose the input matrix by using a non-negative matrix factorization (NMF) algorithm.

In accordance with yet another exemplary embodiment, a non-transitory computer-readable recording medium has a program recorded, the program including command codes that causes a computer device to classify a condition of a patient. When the command codes are executed, the non-transitory computer-readable recording medium causes the computer device to: decompose an input matrix (110) into a sum of a product of a plurality of element matrices (111, 112) and one residual matrix (120) by using a predetermined algorithm, the input matrix representing expression levels of a plurality of genes of a plurality of patients and each of the patients; train a classifier (20) by supervised learning by using a plurality of health condition values representing health conditions of the plurality of patients as learning criteria and inputting the residual matrix into the classifier, in order to train the classifier (20) receiving a matrix having the same dimension as the residual matrix by the supervised learning; and obtain a value for predicting a health condition of a first patient, by inputting a first input matrix including the expression levels of genes of the first patient of which a health condition is required to be predicted into the classifier or inputting a first residual matrix into the classifier, the first residual matrix being a residual matrix obtained from the first input matrix by using the predetermined algorithm.

According one aspect of the present invention, a method of predicting a condition of a patient can be provided. The method comprises: analyzing, by a gene expression level analysis device, expression levels of genes of a first patient of which a health condition is required to be predicted; generating, by a computing device, a first input matrix including the expression levels of genes of the first patient based on the expression levels of genes analyzed for the first patient by receiving the expression levels of genes analyzed for the first patient from the gene expression level analysis device; and obtaining, by the computing device, a value for predicting the health condition of the first patient by inputting the first input matrix into an input layer of a classifier or inputting a first residual matrix into the input layer of the classifier, the classifier being trained by a predetermined supervised learning method, the first residual matrix being a residual matrix obtained from the first input matrix by using a predetermined algorithm.

Here, the predetermined algorithm is an algorithm for decomposing a matrix input to the algorithm into a sum of a product of a plurality of element matrices and one residual matrix.

Here, the predetermined supervised learning method comprises: analyzing, by the gene expression level analysis device, expression levels of genes from respective cells obtained from a plurality of patients; calculating, by the computing device, an input matrix representing the plurality of patients and expression levels of a plurality of genes of each of the patients based on the expression levels of genes analyzed for the plurality of patients, by receiving the expression levels of genes analyzed for the plurality of patients from the gene expression level analysis device;

decomposing, by the computing device, the input matrix into a sum of a product of a plurality of element matrices and one residual matrix by using the algorithm; and training, by the computing device, the classifier by supervised learning by using a plurality of health condition values representing health conditions of the plurality of patients as learning criteria and inputting the residual matrix into the input layer of the classifier, in order to train the classifier receiving a matrix having the same dimension as the residual matrix by the supervised learning.

Examples of a gene expression level analysis device may include a PCR device, a qPCR device, a real-time PCR, or a Qrt PCR device, which are known. Devices related to the gene expression level analysis are disclosed in, for example, Korean patent application Nos. KR-2016-0073379, KR-2017-7010333, KR-2014-0154416, or KR-2007-7013342.

According another aspect of the present invention, a method of predicting a condition of a patient comprises: decomposing, by a computing device, an input matrix into a sum of a product of a plurality of element matrices and one residual matrix by using a predetermined algorithm, the input matrix representing expression levels of a plurality of genes of a plurality of patients and each of the patients; training, by the computing device, a classifier by supervised learning by using a plurality of health condition values representing health conditions of the plurality of patients as learning criteria and inputting the residual matrix into the input layer of the classifier, in order to train the classifier receiving a matrix having the same dimension as the residual matrix by the supervised learning; and obtaining, by the computing device, a value for predicting a health condition of a first patient, by inputting a first input matrix into an input layer of the classifier or inputting a first residual matrix into the input layer of the classifier, the first input matrix including the expression levels of genes of the first patient of which a health condition is required to be predicted, the first residual matrix being a residual matrix obtained from the first input matrix by using the algorithm.

Here, the predetermined algorithm is an algorithm for decomposing a matrix input to the algorithm into a sum of a product of a plurality of element matrices and one residual matrix.

Here, the method may further comprises: analyzing, by the gene expression level analysis device, expression levels of genes of a first patient of which the health condition is required to be predicted; generating, by the computing device, the first input matrix including the expression levels of genes of the first patient based on the expression levels of genes analyzed for the first patient by receiving the expression levels of genes analyzed for the first patient from the gene expression level analysis device; and obtaining, by the computing device, the value for predicting the health condition of the first patient, by inputting the first input matrix into an input layer of the classifier or inputting a first residual matrix into the input layer of the classifier, the first residual matrix being a residual matrix obtained from the first input matrix by using a predetermined algorithm.

Here, the predetermined algorithm may be a non-negative matrix factorization algorithm.

Here, the classifier may be trained by the supervised learning to classify the plurality of patients by receiving the residual matrix and assigning indexes representing different patients included in the input residual matrix to predetermined groups.

Here, each row of the input matrix and the residual matrix may represent a different gene, each column of the input matrix represents a different patient.

Here, each row of the input matrix may represent a different gene, and each column of the input matrix represents a different test sample collected from bodies of the patients, and when patients represented by two different columns of the input matrix are the same patient, the two different columns are test samples collected from different sites of a body of the same patient.

Here, the plurality of element matrices may comprise a total of two element matrices, and the input matrix is the same as a matrix obtained by adding the residual matrix to a product of the two element matrices.

According another aspect of the present invention, a system for predicting a health condition of a patient can be provided. The system comprises a gene expression level analysis device; and a computing device. Here, the gene expression level analysis device is configured to analyze expression levels of genes of a first patient of which a health condition is required to be predicted, and analyze expression levels of genes from respective cells obtained from a plurality of patients. The computing device comprises: a residual generation unit configured to output one residual matrix by receiving an input matrix representing the plurality of patients and expression levels of a plurality of genes of each of the patients and decomposing the input matrix into a sum of a product of a plurality of element matrices and the residual matrix; and a classifier configured to receive a matrix having the same dimension as the residual matrix, the classifier being trained by a predetermined supervised learning method; and a processing unit. Here, the processing unit is configured to: generate a first input matrix including the expression levels of genes of the first patient based on the expression levels of genes analyzed for the first patient, by receiving the expression levels of genes analyzed for the first patient from the gene expression level analysis device; and calculate a value for predicting the health condition of the first patient by inputting the generated first input matrix into an input layer of the classifier, and the predetermined supervised learning method comprises: analyzing, by the gene expression level analysis device, expression levels of genes from respective cells obtained from a plurality of patients; calculating, by the computing device, an input matrix representing the plurality of patients and expression levels of a plurality of genes of each of the patients based on the expression levels of genes analyzed for the plurality of patients, by receiving the expression levels of genes analyzed for the plurality of patients from the gene expression level analysis device; decomposing, by the residual generation unit of the computing device, the input matrix into a sum of a product of a plurality of element matrices and one residual matrix by using a predetermined algorithm; and training, by the computing device, the classifier by supervised learning by using a plurality of health condition values representing health conditions of the plurality of patients as learning criteria and inputting the residual matrix into the input layer of the classifier, in order to train the classifier by the supervised learning.

Here, the computing device may further comprise a user interface, and sizes of the plurality of element matrices may be adjusted according to a parameter value input through the user interface.

Here, the residual generation unit may comprise an equator, and the equator may be configured to decompose the input matrix by using a non-negative matrix factorization (NMF) algorithm.

BRIEF DESCRIPTION OF THE DRAWINGS

FIG. 8A is a flowchart illustrating a method of classifying patients in a computing device in accordance with an exemplary embodiment of the present disclosure;

FIG. 8B is a flowchart illustrating a method of classifying patients in a computing device in accordance with another exemplary embodiment of the present disclosure;

FIG. 11 is a diagram illustrating an example in which a plurality of people are classified into a plurality of groups by a second classifier; and FIG. 12A is a table showing a result of assigning a subtype of a patient according to a subtype assignment method in accordance with an exemplary embodiment of the present disclosure and FIG. 12B is a table showing a result of assigning a subtype of a patient according to a subtype assignment method according to a CMS method, and FIG. 12C is a table showing a result of assigning a subtype of a patient according to a subtype assignment method according to a CRIS method.

DETAILED DESCRIPTION OF EMBODIMENTS

Hereinafter, exemplary embodiments of the present disclosure will be described with reference to the drawings. However, the present disclosure is not limited to the exemplary embodiments described herein, and may be implemented by various modifications. The terms used herein are intended to aid understanding of the exemplary embodiments, and are not intended to limit the scope of the present disclosure. In addition, the singular forms used hereinafter include plural forms unless otherwise clearly expressed.

Figure 1:
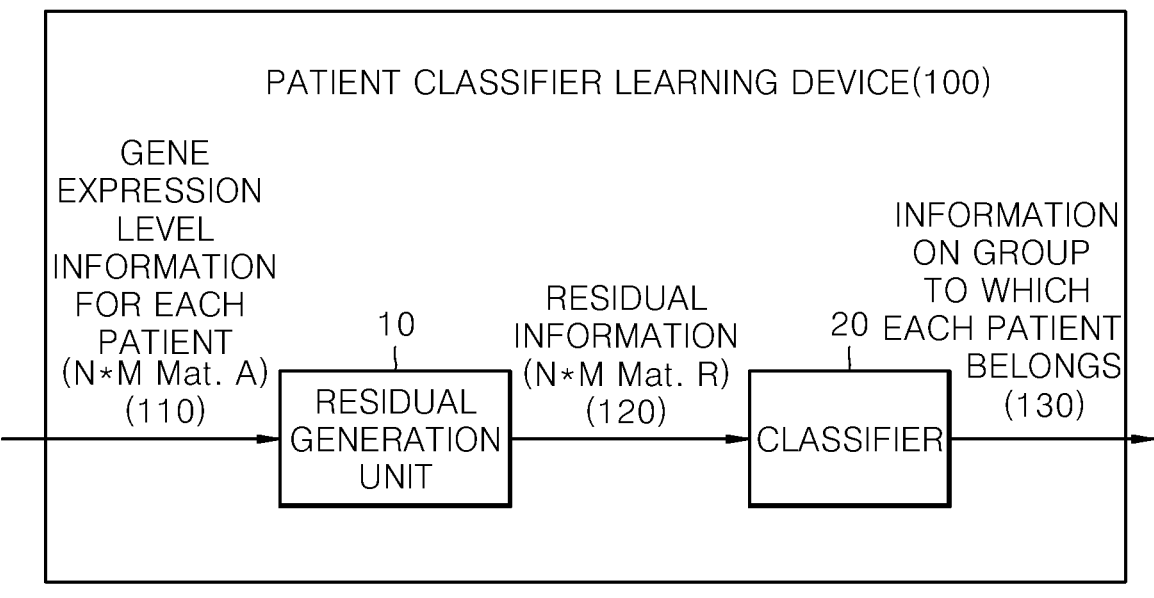
FIG. 1 is a diagram for describing a method of training a classifier for classifying patients in accordance with an exemplary embodiment of the present disclosure.

FIG. 1 is a diagram for describing a method of training a classifier for classifying patients in accordance with an exemplary embodiment of the present disclosure.

A patient classifier learning device 100 may include a residual generation unit 10 and a classifier 20.

The patient classifier learning device 100 may be a general-purpose computing device such as a server or a desktop computer, or a dedicated digital signal processing device for patient classification. When the patient classifier learning device 100 is the general-purpose computing device, the residual generation unit 10 and the classifier 20 may be classified based on a software module. That is, the residual generation unit 10 may be implemented as a first software module and the classifier 20 may be implemented as a second software module.

In contrast, when the patient classifier learning device 100 is the dedicated digital signal processing device, the residual generation unit 10 and the classifier 20 may be separated from each other based on software modules or may be separated from each other in hardware. For example, the residual generation unit 10 may be implemented as a first hardware module and the classifier 20 may be implemented as a second hardware module.

The residual generation unit 10 may receive gene expression level information 110 for each patient. The residual generation unit 10 may output residual information 120 by processing the gene expression level information 110 for each patient. The meaning of the residual information 120 will be described later.

The gene expression level information for each patient may be information obtained from each patient before drug treatment for the patient.

The classifier 20 included in the patient classifier learning device 100 may receive the residual information 120 output from the residual generation unit 10.

The classifier 20 may analyze the residual information 120 and classify a plurality of patients into groups of a predetermined number of predetermined types, and may output information on the group to which each patient belongs.

For example, the groups may include group A having a good prognosis after cancer treatment, group B having a moderate prognosis, and group C having a poor prognosis, as described above.

In this case, the classifier 20 well designed to classify the input data according to the format of the data input to the classifier 20 may be sufficient, and the present disclosure is not completely limited by the specific classification method of the classifier 20. Many techniques for classifying data have been well known, and a technique applicable to the input data type in accordance with the present disclosure may be selected.

In an exemplary embodiment of the present disclosure, the classifier may be a predictive model trained by a supervised learning method. For example, the classifier 20 may be a classifier using a neural network.

When the classifier 20 is trained by the supervised learning method, the correct answer values for the supervised learning may include prognostic values of patients 1 to N that are actually checked by analyzing the health conditions of patients 1 to N when the gene expression level information 110 for each patient includes gene expression level information of patients 1 to N, as described above. The prognostic value may be a value expressed as a number, or the prognostic value may be an index value representing any one of a plurality of pre-presented groups. The prognostic value may also be referred to as a 'learning criterion parameter'. The gene expression level information of patients 1 to N is information on the expression levels of genes before patients 1 to N receives drug treatment.

In an exemplary embodiment of the present disclosure, classification values, which are result values classified by the classifier 20, are obtained by using a set of gene expression level information 110 for each patient for learning, and then the neural network of the classifier 20 may be updated to reduce an error between a set of correct answer values corresponding to a set of gene expression level information 110 for each patient for learning and the obtained classification values. The training state of the classifier 20 may be advanced by repeating the neural network update process multiple times using a plurality of sets of gene expression level information for each patient for learning and a plurality of sets of correct answer values corresponding thereto.

Figure 2:
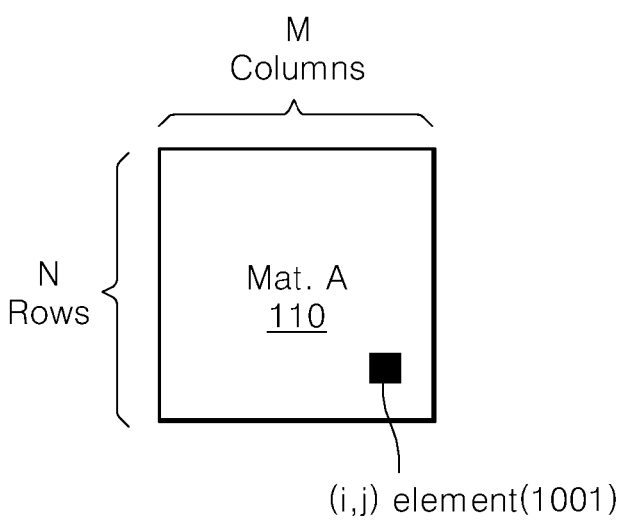
FIG. 2 is a diagram illustrating a format of gene expression level information for each patient input to a patient classifier learning device in accordance with an exemplary embodiment of the present disclosure.

FIG. 2 is a diagram illustrating a format of gene expression level information 110 for each patient input to the patient classifier learning device 100 in accordance with an exemplary embodiment of the present disclosure.

The gene expression level information for each patient may be information obtained from each patient before drug treatment for the patient.

The gene expression level information 110 for each patient may be given as a matrix Mat.A having a size of N (row)*M (column). Hereinafter, a matrix for the gene expression level information 110 for each patient may be referred to as an input matrix 110.

Each row of the input matrix 110 represents the expression level of a gene or transcription factor selected in advance. Each column of the input matrix 110 represents each patient. In addition, the elements (i, j) of the i-th row and the j-th column in the input matrix 110 represent values of the expression level of the i-th gene extracted from the j-th patient.

Figure 3:
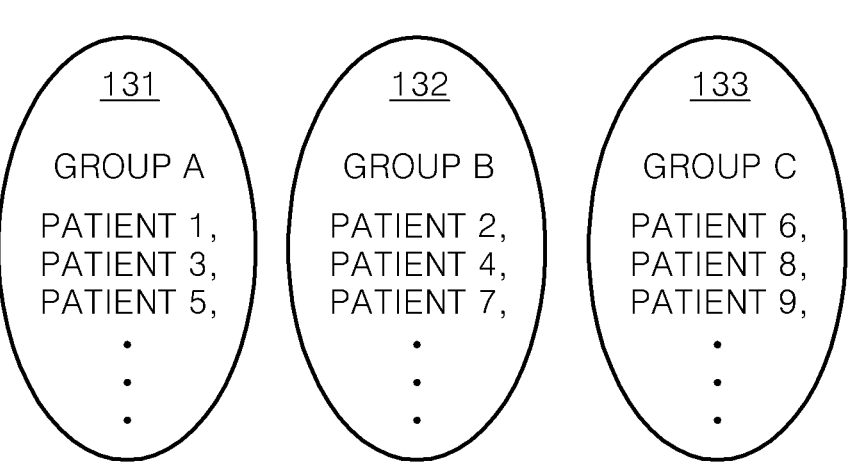
FIG. 3 is a diagram illustrating an example in which a plurality of people are classified into a plurality of groups by a classifier in accordance with an exemplary embodiment of the present disclosure.

FIG. 3 is a diagram illustrating an example in which a plurality of people are classified into a plurality of groups by the classifier 20 of the patient classifier learning device 100 of FIG. 1 in accordance with an exemplary embodiment of the present disclosure.

For example, the input matrix 110 input to the residual generation unit of the patient classifier learning device 100 may include information on the gene expression levels of patients 1 to 9.

Although people are classified into three groups in FIG. 3, the number of groups may be changed according to exemplary embodiments.

In FIG. 3, group A 131 represents a group consisting of people having a good prognosis, group B 132 represents a group consisting of people having a moderate prognosis, and group C 133 represents a group consisting of people having a poor prognosis.

In this case, patient 1, patient 3, and patient 5 may belong to group A 131, patient 2, patient 4, and patient 7 may belong to group B 132, and patient 6, patient 8, and patient 9 may belong to group C 133.

Figure 4:
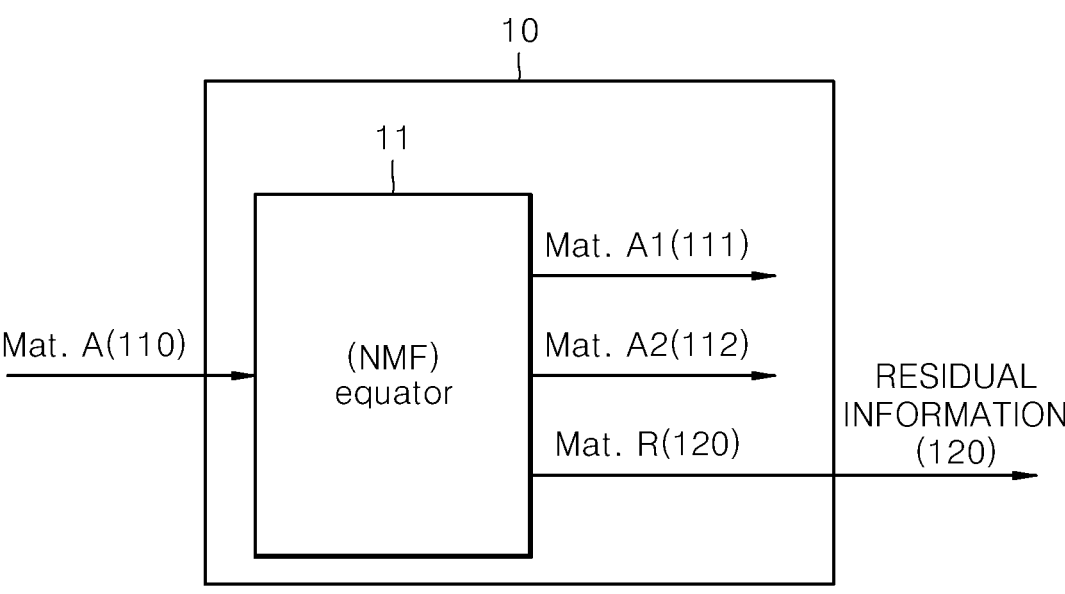
FIG. 4 is a diagram illustrating a configuration of a residual generation unit illustrated in FIG. 1 in more detail in accordance with an exemplary embodiment of the present disclosure.

FIG. 4 is a diagram illustrating a configuration of the residual generation unit 10 illustrated in FIG. 1 in more detail in accordance with an exemplary embodiment of the present disclosure.

The residual generation unit 10 may include an equator 11.

The equator 11 may analyze the input matrix 110 and output it as a product of two matrices and a residual matrix added thereto. In an exemplary embodiment, the equator 11 uses, for example, a non-negative matrix factorization (NMF) algorithm.

More specifically, the input matrix 110 (Mat.A) may be input to the input terminal of the equator 11, and the equator 11 may equivalently decompose the input matrix 110 into a product matrix between a first element matrix 111 (Mat.A1) and a second element matrix 112 (Mat.A2), and a residual matrix 120 (Mat.R) added to the product matrix. Accordingly, the equator 11 may output the residual matrix 120, and as a result, the residual generation unit 10 may output the residual matrix 120 as residual information.

The above-mentioned fact that matrix may be equivalently decomposed using the NMF algorithm is already well known.

In this case, Equation 1 below is established.

$$A = A1 * A2 + R \qquad \text{[Equation 1]}$$

In Equation 1 above, matrix A may be an N*M matrix, matrix A1 may be an N*K matrix, matrix A2 may be a K*M matrix, and matrix R may be a matrix having the same size as matrix A.

Figures 5A, 5B, 5C:
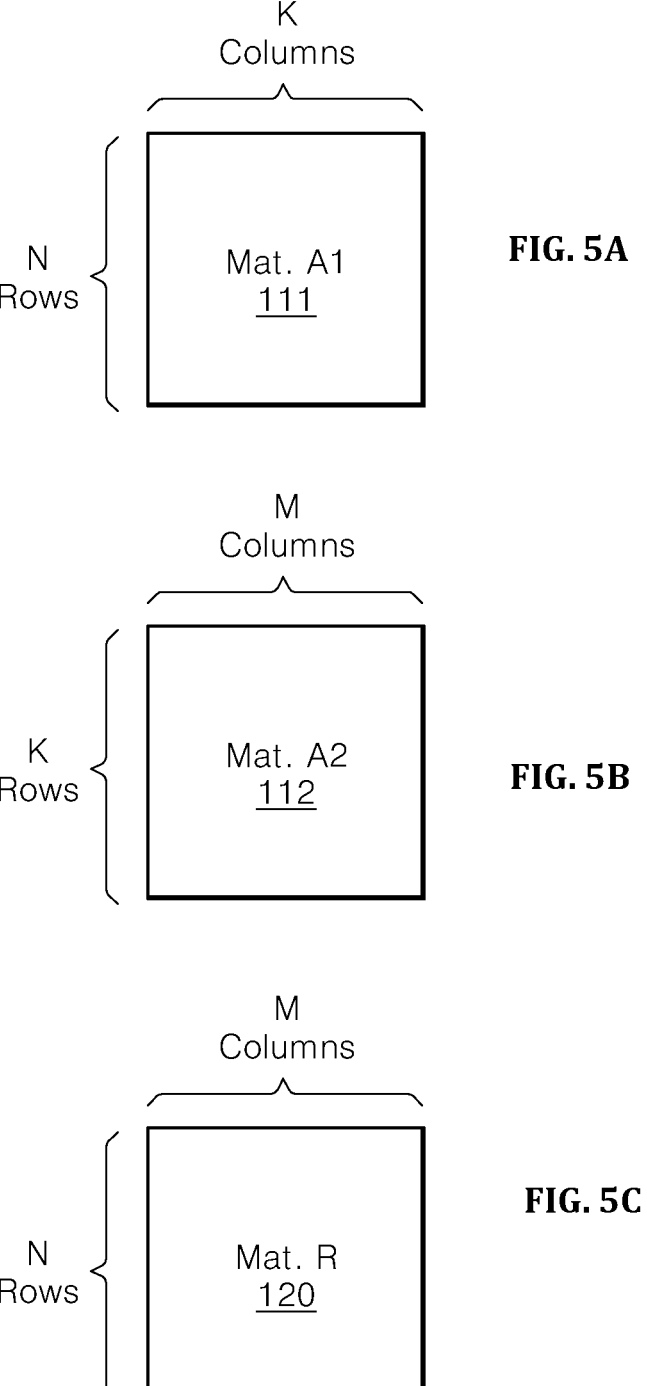
FIGS. 5A, 5B and 5C are diagrams conceptually illustrating sizes of a matrix A1, a matrix A2, and a matrix R in accordance with an exemplary embodiment of the present disclosure.

FIG. 5 is a diagram conceptually illustrating sizes of the matrix A1, the matrix A2, and the matrix R in accordance with an exemplary embodiment of the present disclosure.

Here, the value of K may be set to an optimal value.

In this case, K may be a user-specified parameter.

Figure 6:
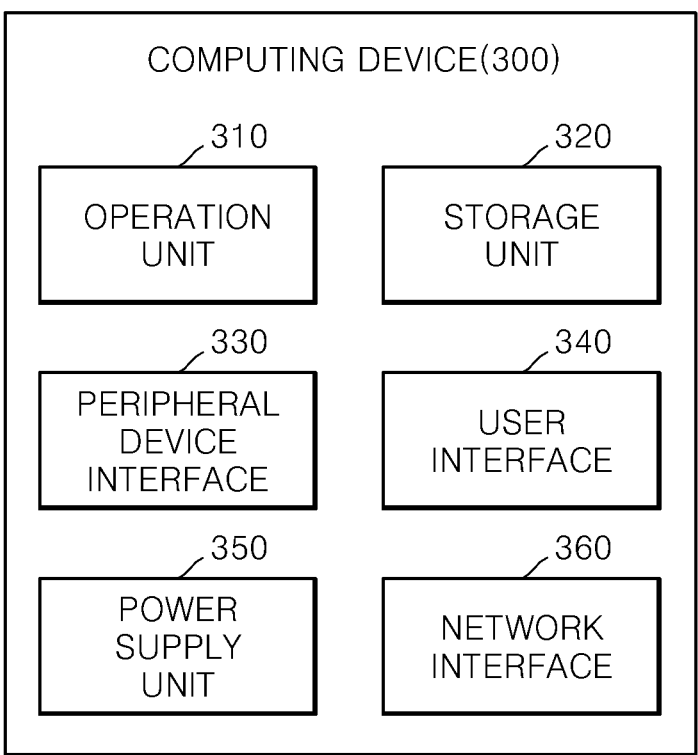
FIG. 6 is a diagram illustrating a structure of a computing device provided in accordance with an exemplary embodiment of the present disclosure.

FIG. 6 is a diagram illustrating a structure of a computing device provided in accordance with an exemplary embodiment of the present disclosure.

The computing device 300 may include an operation unit 310, a program storage unit 320, a peripheral device interface 330, a user interface 340, a power supply unit 350, and a network interface 360.

The operation unit 310 may be, for example, a central processing unit (CPU), a graphic processing unit (GPU), and an application processor (AP) that processes instructions loaded in the operation unit 310.

The storage unit 320 may be a nonvolatile memory that stores a program code composed of a set of the instructions and/or information on the input matrix. For example, it may be a hard disk drive (HDD), and a solid state drive (SDD).

The peripheral device interface 330 may be an interface for connecting an external storage device such as a printer or an SD card. For example, the patient classification result illustrated in FIG. 3 may be output to a printer. Further, the external storage device may take over the role of the storage unit 320.

The user interface 340 may be a keyboard, a mouse, a display device, or the like. For example, the patient classification result illustrated in FIG. 3 may be output on a screen of a display device.

The power supply unit 350 is a device that supplies operating power to the computing device 300 and may include a battery.

The network interface 360 may be a device provided for communication with an external device separated from the computing device 300. The program code and/or information on the input matrix may be provided through the network interface 360.

In this case, the patient classifier learning device 100 illustrated in FIG. 1 may refer to the computing device 300 illustrated in FIG. 6.

The residual generation unit 10 and the classifier 20, which are illustrated in FIG. 1, may be conceptualized representation of a functional configuration formed by loading the program code in the operation unit 310 and executing the loaded program code.

In addition, the computing device 300 may be a device including a digital signal processing board, and may be implemented such that the functions of the residual generation unit 10 and the classifier 20 are performed in different physical regions.

Figure 7A:
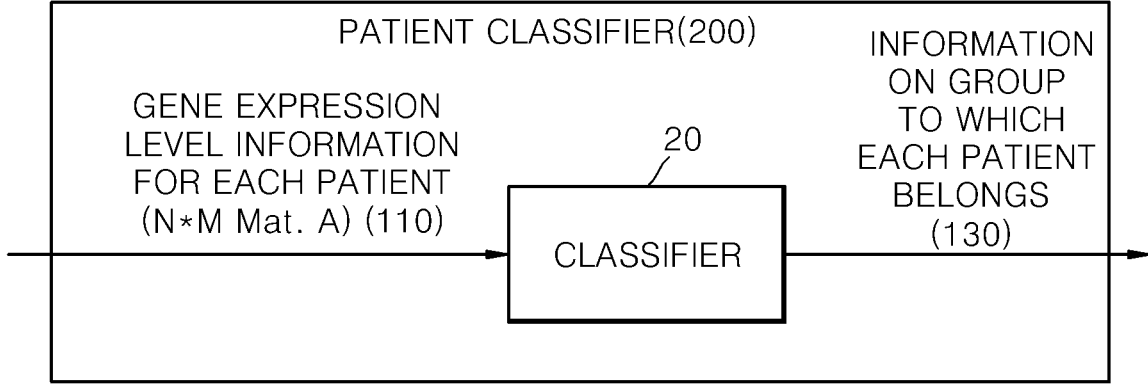
FIGS. 7A and 7B are a flowchart illustrating a method of classifying patients in a computing device in accordance with an exemplary embodiment of the present disclosure.
Figure 7B:
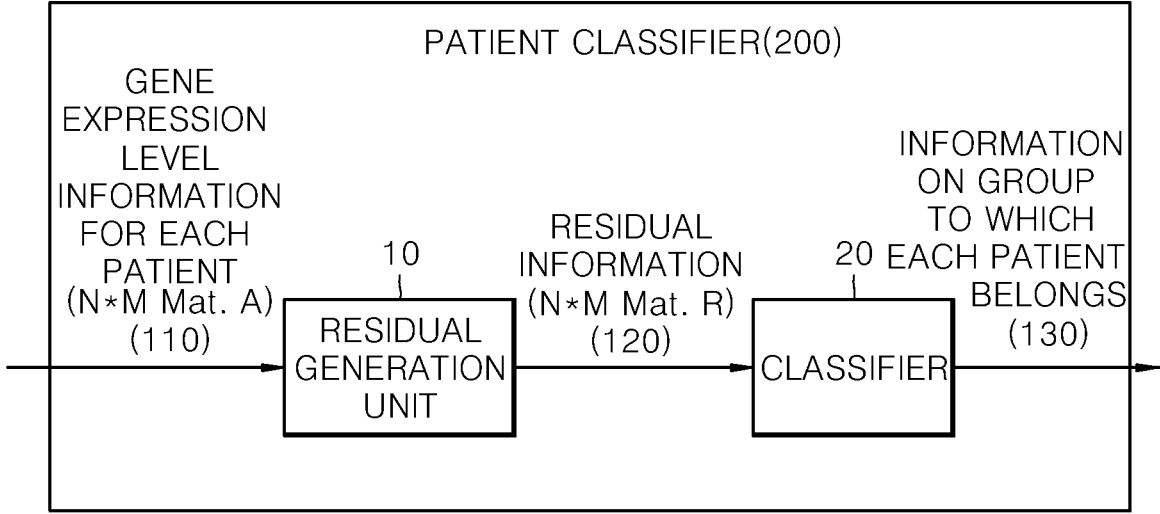

FIG. 7 is a flowchart illustrating a method of classifying patients in a computing device in accordance with an exemplary embodiment of the present disclosure.

The computing device may include a hardware module or a software module that may be defined as a patient classifier 200.

In an exemplary embodiment illustrated in part (a) of FIG. 7, the patient classifier 200 may include the classifier 20 trained through the process described in FIG. 1.

In the classifier 20, gene expression level information 110' for each patient that is actually required to be classified may be directly input. The gene expression level information 110' for each patient may have the same format as the gene expression level information 110 for each patient illustrated in FIG. 1.

The gene expression level information for each patient may be information obtained from each patient before drug treatment for the patient.

Although the classifier 20 trained in FIG. 1 is trained using the residual information 120, the classifier 20 may successfully assign the patient to the correct group, even if the gene expression level information 110' for each patient itself, not the residual information generated from the gene expression level information 110' for each patient, is input to the trained classifier 20.

The residual information is the remaining information derived through an NMF operation. Therefore, the remaining information may be obtained only through the NMF operation result, and may also be changed by the specific value of K, which is a user-specified parameter. Therefore, for universal application of the learner, it may be appropriate to input the original information on patient gene expression levels rather than using residual information.

In another exemplary embodiment illustrated in part (b) of FIG. 7, the patient classifier 200 may include the classifier 20 trained through the process described in FIG. 1 and the residual generation unit 10 described above. Residual information 120' may be generated from the gene expression level information 110' for each patient by using the residual generation unit 10, and the generated residual information 120' may be input to the classifier 20. Since the classifier 20 trained in FIG. 1 is trained by using the residual information 120, the classifier 20 may successfully assign the patient to the correct group by inputting the residual information 120' into the classifier 20.

FIG. 8A is a flowchart illustrating a method of classifying patients in a computing device in accordance with an exemplary embodiment of the present disclosure.

In step S10, the input matrix 110 representing an expression level of each of a plurality of (N) genes for each of a plurality of (M) patients may be prepared.

In step S20, a plurality of patients represented by the input matrix 110 may be classified by inputting the prepared input matrix 110 to the classifier 20 trained through the process of FIG. 1.

FIG. 8B is a flowchart illustrating a method of classifying patients in a computing device in accordance with another exemplary embodiment of the present disclosure.

In step S110, the input matrix 110 representing an expression level of each of a plurality of (N) genes for each of a plurality of (M) patients may be prepared.

In step S120, the input matrix 110 may be decomposed into a sum of the product of the plurality of matrices 111 and 112 and one residual matrix 120.

In step S130, a plurality of patients represented by the input matrix 110 may be classified by inputting the residual matrix 120 to the classifier 20 trained through the process of FIG. 1.

Figure 9:
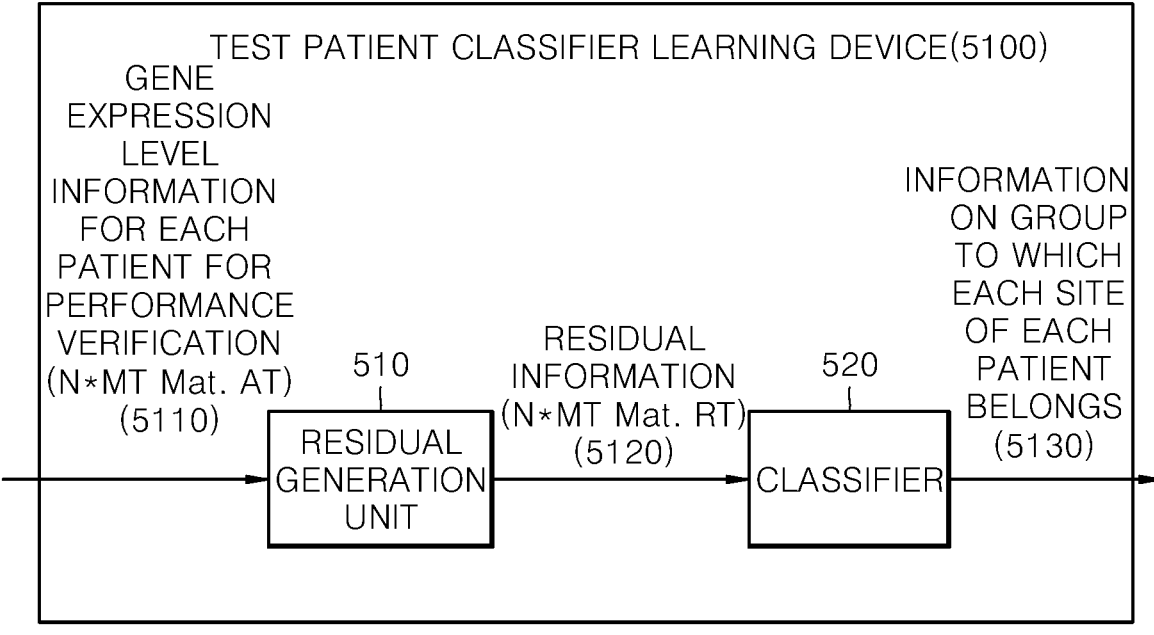
FIG. 9 is a diagram for describing a test patient classifier learning method and a test patient classifier learning device presented to prove the advantageous effect of the method of classifying patients described in FIG. 1 in accordance with an exemplary embodiment of the present disclosure.
Figure 10:
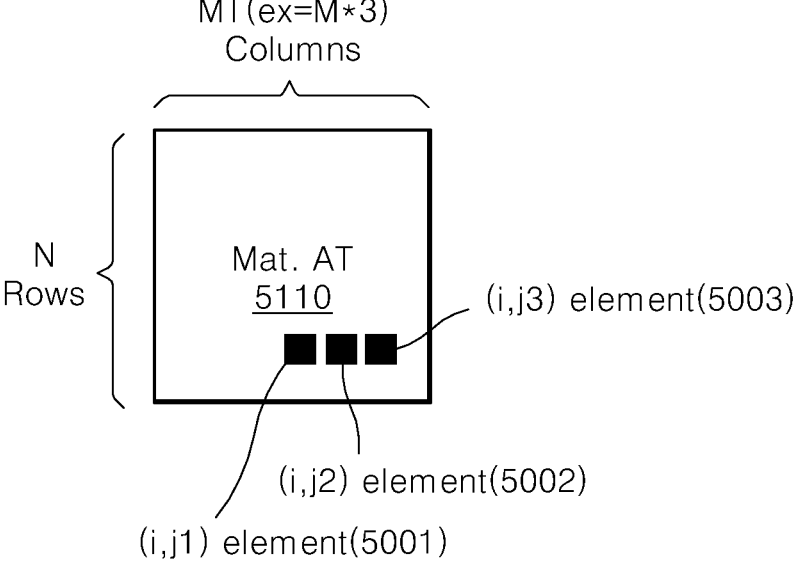
FIG. 10 is a diagram for describing a format of a second input matrix of FIG. 8 in accordance with an exemplary embodiment of the present disclosure.

FIGS. 9 to 11 illustrate a test method for proving that the present disclosure illustrated in FIG. 1 can obtain an advantageous effect in accordance with an exemplary embodiment.

FIG. 9 is a diagram for describing a test patient classifier learning method and a test patient classifier learning device 5100 presented to prove the advantageous effect of the method of classifying patients described in FIG. 1 in accordance with an exemplary embodiment of the present disclosure.

The test patient classifier learning apparatus 5100 may include a second residual generation unit 510 and a second classifier 520.

The second residual generation unit 510 may receive the second input matrix 5110 (AT) and may output second residual information 5120 (RT). In this case, the second input matrix 5110 may be a matrix regarding information on the gene expression levels for each patient for performance verification.

The second input matrix 5110, the second residual generation unit 510, the second residual information 5120, and the second classifier 520 illustrated in FIG. 9 correspond to the input matrix 110, the residual generation unit 10, the residual information 120, and the classifier 20 illustrated in FIG. 1, respectively.

FIG. 10 is a diagram for describing the format of the second input matrix 5110 of FIG. 8 in accordance with an exemplary embodiment of the present disclosure.

The second input matrix 5110 may be gene expression level information for each patient.

The second input matrix 5110 may be a matrix having a size of N*MT. In this case, each row of the second input matrix 5110 may represent a preset gene. In addition, each column of the second input matrix 5110 may represent a specific body site of a specific patient. In this case, two different columns may represent different patients. If two different columns represent the same patient, then the two different columns may represent different body sites of the same patient.

For example, the (i, j1) element is a value related to the expression level of gene I extracted from the first site of patient j, the (i, j2) element is a value related to the expression level of gene I extracted from the second site of patient j, and the (i, j3) element may be a value related to the expression level of gene I extracted from the third site of patient j.

In the example illustrated in FIG. 10, MT is the value that is three times M illustrated in FIG. 1. In FIG. 9, it is illustrated that the amount of genes extracted from three different body sites for each patient is used. However, the second input matrix 5110 illustrated in FIG. 10 may be differently constructed.

As compared to the input matrix 110, the second input matrix 5110 illustrated in FIG. 10 has the same number of rows, but differs in that the number of columns is increased. The second residual generation unit 510 and the second classifier 520 of FIG. 9 may perform the same functions as the residual generation unit 10 and the classifier 20 of FIG. 1. The second residual generation unit 510 may generate the second residual information 5120 by decomposing the second input matrix 5110 into a form as shown in Equation 2 below.

$$AT=AT1*AT2+RT \qquad \text{[Equation 2]}$$

In Equation 2 above, matrix AT may be an N*MT matrix, matrix AT1 may be an N*K matrix, matrix AT2 may be a K*MT matrix, and matrix R may be a matrix having the same size as matrix AT.

It is to be understood that the second classifier 520 illustrated in FIG. 9 may be trained in the same manner as in the classifier 20 of FIG. 1. However, the dimension of the matrix information received by the second classifier 520 is only different from the dimension of the matrix information received by the classifier 20.

FIG. 11 is a diagram illustrating an example in which a plurality of people are classified into a plurality of groups by the second classifier 520.

Although people are classified into three groups in FIG. 11, the number of groups may be changed according to exemplary embodiments.

In FIG. 11, group A 5131 represents a group consisting of people having a good prognosis, group B 5132 represents a group consisting of people having a moderate prognosis, and group C 5133 represents a group consisting of people having a poor prognosis.

In FIG. 11, patient 1, patient 3, and patient 5 may belong to group A 5131, patient 2, patient 4, and patient 7 may belong to group B 5132, and patient 6, patient 8, and patient 9 may belong to group C 5133.

In this case, it should be noted that, in accordance with the present disclosure, analysis results using different body sites of a specific patient appear to belong to the same group.

In contrast, when the present disclosure is not used, if even the body samples obtained from the same patient are samples from different sites, in many cases, it may be found that the same patient belongs to two different groups as the analysis result of the two collected samples. Therefore, from the above, it is possible to understand the differential technical effect in accordance with the present disclosure.

Effect in Accordance with the Present Disclosure

Hereinafter, 'RS' in the Table shown in FIG. 12A represents a subtype assignment method according to an exemplary embodiment of the present disclosure, and 'CMS' in the table shown in FIG. 12B represents the most common subtype assignment method for colorectal cancer classification. In addition, 'CRIS' in the table shown in FIG. 12C represents a method of assigning subtypes using an experiment (patient derived xenograft (PDX)) capable of extracting only cancer cell intrinsic information.

FIG. 12A is a table showing a result of assigning a subtype of a patient according to a subtype assignment method in accordance with an exemplary embodiment of the present disclosure and FIG. 12B is a table showing a result of assigning a subtype of a patient according to a subtype assignment method according to a CMS method, and FIG. 12C is a table showing a result of assigning a subtype of a patient according to a subtype assignment method according to a CRIS method.

According to the related art, it is not possible to provide consistent prognostic values for individual patients since different cancer tissues have different gene expression levels. However, considering the data presented in FIG. 12A, FIG. 12B, and FIG. 12C, it is to be understood that consistent prognostic values may be effectively provided by using the present disclosure.

The table shown in FIG. 12A may be interpreted as follows. That is, A to Y refers to a total of 24 different patients. RS1, RS2, RS3 and RS4 refer to each subtype. Gene expression data collected from three different cancer tissues for each patient are prepared, and one for each expression data, a total of three subtypes may be found. Only when the subtypes assigned to one patient match, the subtype assignment method may be considered to be stable. To this end, categories called Q1 and Q2 are created, and it may be evaluated whether subtype assignments are consistent by using Q1 and Q2.

The index, 'Q1', has a value of Yes (Y) or No (N) as an answer to a question of obtaining a subtype matching all of the gene expression data of different cancer tissues of three sites of one patient.

The index, 'Q2', has a value of Yes (Y) or No (N) as an answer to a question of obtaining a subtype matching at least two pieces of the gene expression data of different cancer tissues of three sites of one patient.

In FIG. 12A, 12 out of 24 patients meet the criterion for the index of 'Q1', and 24 of 24 patients meet the criterion for the index of 'Q2'.

In FIG. 12B, CMS1, CMS2, CMS3, and CMS4 refer to each subtype. In FIG. 12B, 4 out of 24 patients meet the criterion for the index of 'Q1', and 22 of 24 patients meet the criterion for the index of 'Q2'.

In FIG. 12C, CRISA, CRISB, CRISC, CRISD, CRISE refer to each subtype. In FIG. 12C, 10 out of 24 patients meet the criterion for the index of 'Q1', and 21 of 24 patients meet the criterion for the index of 'Q2'.

As can be seen through FIG. 12A, FIG. 12B, and FIG. 12C, it may be confirmed that the present method consistently shows better performance compared to other methods.

Figure 13:
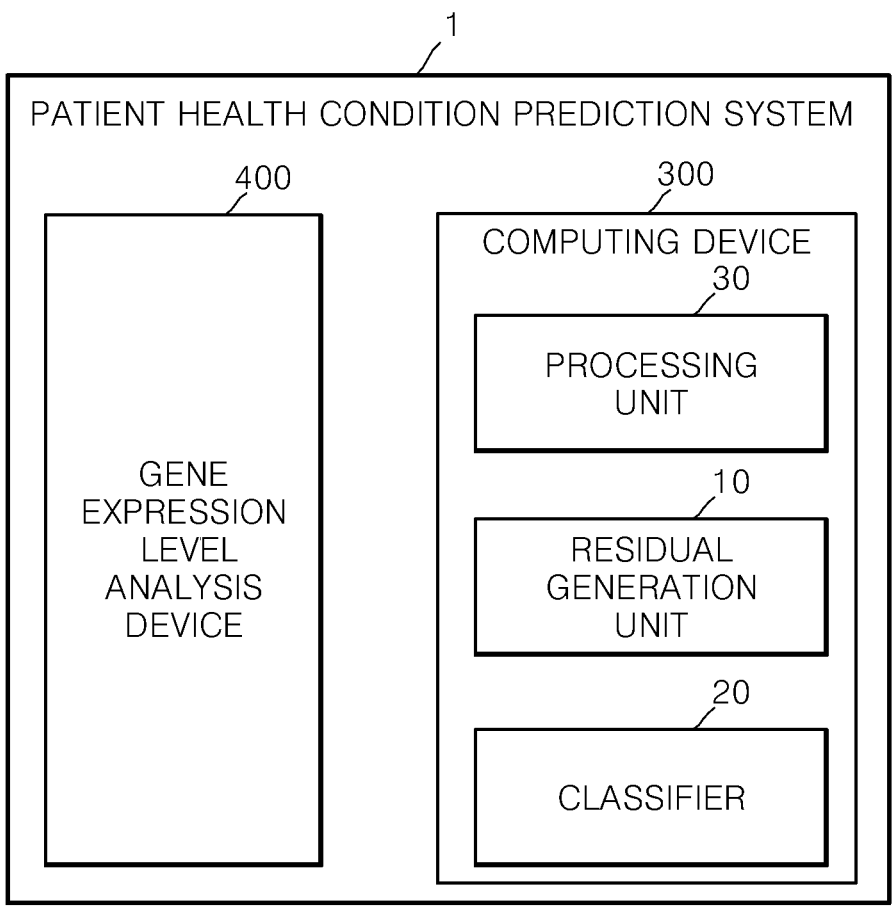
FIG. 13 is a diagram illustrating a configuration of a patient health condition prediction system provided in accordance with an exemplary embodiment of the present disclosure.

FIG. 13 is a diagram illustrating a configuration of a patient health condition prediction system provided in accordance with an exemplary embodiment of the present disclosure.

The health condition prediction system 1 of patients may include a gene expression level analysis device 400 and the computing device 300.

The gene expression level analysis device 400 may be configured to analyze expression levels of genes of a first patient of which a health condition is required to be predicted, and analyze expression levels of genes from respective cells obtained from a plurality of patients.

The computing device 300 may include a residual generation unit 10 configured to output a residual matrix by receiving an input matrix representing the plurality of patients and expression levels of a plurality of genes of each of the patients and decomposing the input matrix into a sum of a product of a plurality of element matrices and one residual matrix; a classifier 20 configured to receive a matrix having the same dimension as the residual matrix, the classifier being trained by a predetermined supervised learning method; and a processing unit 30.

The processing unit 30 may be configured to generate a first input matrix including the expression levels of genes of the first patient based on the expression levels of genes analyzed for the first patient, by receiving the expression levels of genes analyzed for the first patient from the gene expression level analysis device 400. In addition, the processing unit 30 may be configured to calculate a value for predicting the health condition of the first patient by inputting the generated first input matrix into an input layer of the classifier 20.

In this case, the predetermined supervised learning method may include the following steps S10, S20, and S30.

In step S10, the gene expression level analysis device 400 may analyze expression levels of genes of each cell obtained from a plurality of patients, and the computing device 300 may calculate an input matrix representing the plurality of patients and expression levels of a plurality of genes of each of the patients based on the expression levels of genes analyzed for the plurality of patients, by receiving the expression levels of genes analyzed for the plurality of patients from the gene expression level analysis device 400.

In step S20, the residual generation unit 10 of the computing device 300 may decompose the input matrix into a sum of a product of a plurality of element matrices and one residual matrix by using a predetermined algorithm.

Furthermore, in step S30, the computing device 300 may train the classifier 20 by supervised learning by using a plurality of health condition values representing health conditions of the plurality of patients as learning criteria and inputting the residual matrix into the input layer of the classifier 20, in order to train the classifier 20 by supervised learning.

According to the present disclosure, it is possible to provide a technology for reliably classifying a condition of a patient regardless of a sample collection position in the body of the patient.

By using the embodiments of the present disclosure described above, those skilled in the technical field to which the present disclosure belongs could easily implement various changes and modifications without departing from the scope of the essential characteristics of the present disclosure. Features of each claim in Claims may be incorporated into other claims that do not depend on or are not depended on by the claim, within the scope that could be understood upon reading the present specification.

What is claimed is:
1. A method of predicting a condition of a patient, comprising:
  analyzing, by a gene expression level analysis device, expression levels of genes of the patient to obtain a first input matrix, a column of the first input matrix corresponding to the expression levels of genes of the patient; and
  obtaining, by a computing device, a value for predicting the health condition of the patient by inputting the column of the first input matrix into an input layer of a classifier using a neural network, wherein the classifier has been trained using a residual matrix obtained from gene expression data of a plurality of patients, such that the classifier is capable of assigning a same group to test samples collected from different sites of a body of a same patient;
  wherein the classifier has been trained by a predetermined supervised learning method,
  wherein the predetermined supervised learning method comprises:
    analyzing, by the gene expression level analysis device, expression levels of genes from respective cells obtained from a second plurality of patients;
    calculating, by the computing device, a second input matrix representing gene expression levels for the second plurality of patients, by receiving the expres- sion levels of genes analyzed for the second plurality of patients from the gene expression level analysis device;

decomposing, by the computing device, the second input matrix into a sum of a product of a plurality of element matrices and a second residual matrix by using a non-negative matrix factorization (NMF) algorithm; and training, by the computing device, the classifier by supervised learning by using health condition as learning criteria and inputting the second residual matrix into the input layer of the classifier, wherein the non-negative matrix factorization (NMF) algorithm decomposes a given matrix into a sum of a product of a plurality of element matrices and one residual matrix, and wherein the second residual matrix represents information that is different from a product of the plurality of element matrices.

2. A method of predicting a health condition of a patient, comprising:

analyzing, by a gene expression level analysis device, expression levels of genes from respective cells obtained from a second plurality of patients to obtain a second input matrix representing gene expression levels for the second plurality of patients;

decomposing, by a computing device, the second input matrix into a sum of a product of a plurality of element matrices and a second residual matrix by using a non-negative matrix factorization (NMF) algorithm, wherein the second residual matrix is a matrix having the same size as the second input matrix and is different from a product of the plurality of element matrices;

training, by the computing device, a classifier using a neural network by a supervised learning method by using health condition as learning criteria and inputting the second residual matrix into the input layer of the classifier, wherein the classifier is trained such that test samples collected from different sites of a body of a same patient are assigned to a same group; and obtaining, by the computing device, a value for predicting the health condition of the patient, by inputting a column of a first input matrix into the input layer of the trained classifier, the column of the first input matrix including expression levels of genes of the patient, wherein the non-negative matrix factorization (NMF) algorithm decomposes a given matrix into a sum of a product of a plurality of element matrices and one residual matrix.

3. The method of claim 2, wherein the classifier is trained by the supervised learning method to classify the second plurality of patients by receiving the second residual matrix and assigning indexes representing different patients included in the second residual matrix to predetermined groups.

4. The method of claim 2, wherein each row of the second input matrix and the second residual matrix represents a different gene, and each column of the second input matrix represents a different patient.

5. The method of claim 2, wherein each row of the second input matrix represents a different gene, and each column of the second input matrix represents a different test sample collected from bodies of the second plurality of patients, and when patients represented by two different columns of the second input matrix are the same patient, the two different columns are test samples collected from different sites of a body of the same patient.

6. The method of claim 2, wherein the plurality of element matrices comprises a total of two element matrices, and the second input matrix is the same as a matrix obtained by adding the second residual matrix to a product of the two element matrices.

7. A system for predicting a health condition of a patient, comprising:

a gene expression level analysis device; and a computing device, wherein the gene expression level analysis device is configured to analyze expression levels of genes of the patient and analyze expression levels of genes from respective cells obtained from a given plurality of patients, the computing device comprises:

a residual generation unit configured to output a residual matrix by receiving an input matrix representing the expression levels of genes for each of the given plurality of patients and decomposing the input matrix into a sum of a product of a plurality of element matrices and a residual matrix, wherein the residual matrix is a matrix having the same size as the input matrix and is different from a product of the plurality of element matrices; and a classifier using a neural network, and the classifier being trained by a predetermined supervised learning method, wherein the classifier is trained such that test samples collected from different sites of a body of a same patient are assigned to a same group; and a processing unit, the processing unit is configured to:

generate a first input matrix including a column corresponding to the expression levels of genes of the patient; and calculate a value for predicting the health condition of the patient by inputting the column of the generated first input matrix into an input layer of the classifier, and the predetermined supervised learning method comprises:

analyzing, by the gene expression level analysis device, expression levels of genes from respective cells obtained from a second plurality of patients;

calculating, by the computing device, a second input matrix representing gene expression levels for the second plurality of patients by receiving the expression levels of genes analyzed for the second plurality of patients from the gene expression level analysis device, decomposing, by the residual generation unit of the computing device, the second input matrix into a sum of a product of a plurality of element matrices and a second residual matrix by using a predetermined non-negative matrix factorization (NMF) algorithm; and training, by the computing device, the classifier by supervised learning by using health condition as learning criteria and inputting the second residual matrix into the input layer of the classifier.

8. The system of claim 7, wherein the computing device further comprises a user interface, and sizes of the plurality of element matrices are adjusted according to a parameter value input through the user interface.

9. The system of claim 7, wherein the residual generation unit comprises an equator, and the equator is configured to decompose the input matrix by using the non-negative matrix factorization (NMF) algorithm.

* * * * *